United States Patent [19]

Fang

[11] Patent Number: 5,543,097
[45] Date of Patent: Aug. 6, 1996

[54] METHODS FOR PREPARING POLYACRYLAMIDE GELS FOR ELECTROPHORETIC ANALYSIS

[76] Inventor: Ta-Yun Fang, 13755 NW. Burton St., Portland, Oreg. 97229

[21] Appl. No.: 209,632

[22] Filed: Mar. 9, 1994

[51] Int. Cl.[6] .............................. G01N 27/26; B29C 39/02
[52] U.S. Cl. ........................ 264/102; 204/467; 204/470; 204/619; 206/222; 264/299
[58] Field of Search ........................... 204/182.8, 299 R; 264/299, 102, 101; 206/219, 222

[56] References Cited

U.S. PATENT DOCUMENTS

| | | | |
|---|---|---|---|
| 3,156,369 | 11/1964 | Bowes et al. | 206/222 |
| 3,802,604 | 4/1974 | Morane et al. | 206/222 |
| 3,968,872 | 7/1976 | Cavazza | 206/222 |
| 4,294,351 | 10/1981 | Cheetham | 206/222 |
| 4,750,615 | 6/1988 | Kaufeler | 206/222 |
| 4,762,743 | 8/1988 | von Alven et al. | 204/182.8 |
| 4,820,398 | 4/1989 | Yamamoto | 204/182.8 |
| 4,903,865 | 2/1990 | Janowitz | 206/222 |
| 4,954,236 | 9/1990 | Kushner et al. | 204/182.8 |
| 5,038,951 | 8/1991 | Rizzardi | 206/222 |
| 5,170,888 | 12/1992 | Goncalves | 206/222 |
| 5,192,408 | 3/1993 | Scott | 204/182.8 |
| 5,228,970 | 7/1993 | Foley | 204/182.8 |
| 5,232,573 | 8/1993 | Rosenvold | 204/182.8 |
| 5,246,142 | 9/1993 | DiPalma et al. | 206/222 |
| 5,384,025 | 1/1995 | Blasband | 204/299 R |

OTHER PUBLICATIONS

Methods in Molecular Biology, vol. 1, *Proteins*, Edited by John M. Walker, SDS Polyacrylamide Gel Electrophoresis of proteins, Author—B.J. Smith pp. 41–54 (Humana Press—Clifton New Jersey).
*Cleavage of Structural Proteins during the Assembly of the Head of Bacteriophage T4* by U.K. Laemmli; Nature Vo. 227, Aug. 15, 1970.
*Disc Electrophoresis—II, Method and Application to Huan Serum Proteins*, Author: Baruch J. Davis, pp. 404–427, (1964).
*Acrylamide Gel Mixtures*, Owl Scientific, Inc. pp. 144–145.
*Accessories for Vertical Slab Gel Systems*, C.B.S. Scientific Company, Inc., p. 25.
*Joey Gel Casting System*, Owl Scientific, Inc. pp. 42–43.
*Mini–Protean II Dual Slab Cell, Instruction Manual*, (Bio–Rad Laboratories), pp. 8–14.
*DNA Sequencing—Poker Face II Nucleic Acid Sequenceer* (Hoefer Scientific Instruments) p. 37.
Electrophoresis: *Vertical Gels* (Hoefer Scientific Instruments) p. 50.

Primary Examiner—Mathieu D. Vargot
Attorney, Agent, or Firm—Marger Johnson McCollom & Stolowitz, P.C.

[57] ABSTRACT

This invention relates to a method and system for producing a polyacrylamide gel sample typically for use in electrophoretic analysis. The subject method includes providing a container comprising a bottle and cap assembly for conducting a gel formation sequence. The cap assembly includes a storage compartment. A plurality of premixed chemical materials are employed for producing a polyacrylamide gel used to make the gel samples. The container includes a bottle for storing an acrylamide solution and a cap assembly for storing the premixed chemical materials in dry particulate form therewithin. The cap is located atop the bottle. The premixed chemical materials are stored in the bottle and in the storage compartment for subsequently producing the acrylamide gel solution in situ within the confines of the container so that the step of transferring of the gel stock solutions to an auxiliary container is avoided. A polyacrylamide gel sample for use in electrophoretic analysis can be produced from the above-described acrylamide gel solution. The sample is produced within a leak-proof formation chamber typically includes a pair of plates and a easily-alignable, unitary, substantially U-shaped spacer member.

15 Claims, 5 Drawing Sheets

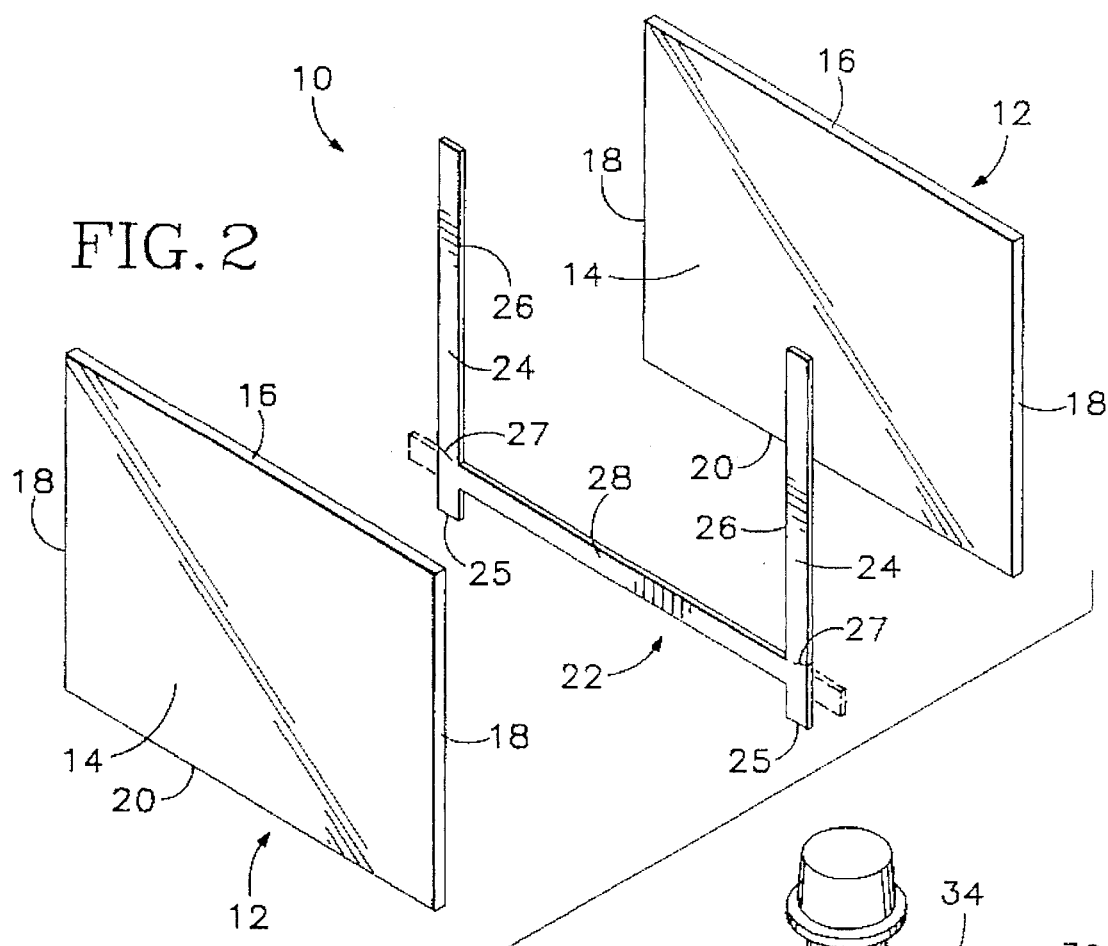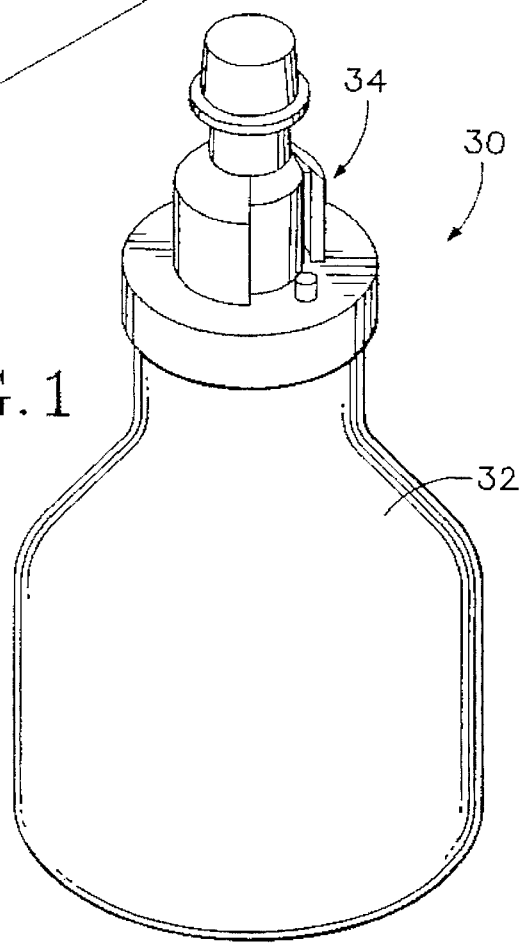

METHODS FOR PREPARING POLYACRYLAMIDE GELS FOR ELECTROPHORETIC ANALYSIS

BACKGROUND OF THE INVENTION

This invention relates to methods for preparing acrylamide gels for electrophoretic analysis, and more particularly to methods for producing acrylamide gel solutions and then forming these solutions into polyacrylamide gel samples for electrophoretic analysis.

Polyacrylamide gel electrophoresis (PAGE) is a powerful technique commonly used in biochemistry and biomedicine research. Depending on the purpose, this technique can be used to perform either analytical or preparative studies of protein and nucleic acid. A book (article) entitled "SDS Polyacrylamide Gel Electrophoresis of Proteins" by B. J. Smith, relates to PAGE. The following are some of the common applications of PAGE which are used in protein chemistry and molecular biology:

1. Protein molecular weight determination.
2. Monitoring protein purification.
3. Preparative protein isolation.
4. Nucleic acid separation.
5. DNA sequencing.

PAGE was first introduced to the field of protein analysis more than twenty years ago. The most widely used PAGE procedure is that of Laemmli (1970). Electrophoretic separation of biological molecules on polyacrylamide gel is based on the net charge, shape and size of these molecules. These gels are typically formed by the polymerization of an acrylamide monomer solution. The process is initiated by adding a free radical-generating compound into the acrylamide solution. Gels are made with different concentration of acrylamide and cross linked by adding initiator (such as ammonium persulfate) and an accelerator, for example, tetramethyl-ethylenediamine (TEMED). A detergent, such as sodium dodecyl sulfate (SDS), or urea are incorporated into the gel if samples are analyzed under dissociation conditions.

Probably the most widely used of techniques for analyzing mixtures of proteins is SDS polyacrylamide gel electrophoresis. In this technique, proteins are reacted with the anionic detergent SDS, or sodium lauryl sulfate, to form negatively charged complexes. The amount of SDS bound by a protein, and so the charge on the complex, is roughly proportional to its size. Commonly, about 1.4 g. SDS is bound per 1 g. protein, although there are exceptions to this rule. The proteins are generally denatured and solubilized by their binding of SDS, and the complex forms a prolate ellipsoid or rod of a length roughly proportionate to the protein's molecular weight. Thus, proteins of either acidic or basic form negatively charged complexes that can be separated on the bases of difference in sizes by electrophoresis through a sieve-like matrix of polyacrylamide gel.

SDS-polyacrylamide gel electrophoresis is reproducible, versatile, and convenient. It uses either a tubular disc gel or a slab gel. The slab gel technique is an improvement of the disc gel electrophoresis. Less gel and sample materials are required per assay on a slab gel system, and the resulting gel can be easily used for further analysis. Electrophoresis on slab gel of full size (~16–20×16 cm), or mini-size (~10×10 cm) of 1.5 mm, 1.0 mm, 0.75 mm and even 0.5 mm thickness, is made with composition described by Davis (1964) and by Laemmli. The gel is typically prepared at an acrylamide concentration of 15%, 12%, 10%, 8% or 7.5% or of a gradient in concentration ranging from 5% to 20%. Often, a 4% stacking gel is casted on the top portion of the gel to facilitate good separations.

The conventional method to make slab polyacrylamide gel is by casting a polymeric gel between a pair of glass plates. Thus, the initiator-containing acrylamide gel solution is cast in the rectangular cavity formed between the two glass plates. The thickness of the gel is determined by the thickness of spacers inserted between the glass plates which form the cavity therebetween. The assembly uses two or three spacers made of plastic strips. These spacers can be 1 cm wide and 1.5, 1.0, 0.75 and 0.5 mm thick. Two of them serve as side spacers and are laid on the sides of glass plates. They have the same length as the height of longer bottom plate. If a third spacer is used, it is positioned below the side spacers on the bottom of the glass plate and is a little longer than the width of the plate. The whole set-up is held in place with either clamps or specially made holders. Warm agar solution, tape, or special gel casting stand are some of the ways to seal any possible leakage. Acrylamide gel solution with TEMED added is poured into the space between glass plates. The gel forms after the acrylamide polymerization is completed. The bottom spacer portion is then removed from the assembly. To carry out electrophoresis, the lower part of the gel sits in a buffer bath and the top part of the gel is enclosed by a top buffer bath. Then, current is applied to the system to separate molecules of protein or nucleic acid.

There are, however, a number of disadvantages to the above-described conventional process. First, assembling plates and spacers for casting polyacrylamide gel is a cumbersome and time consuming process. Even with a special casting stand, a certain degree of manipulation is required in order to put the assembly together. Second, the cost of the electrophoresis system including a gel casting system is expensive, and parts from different system are not interchangeable. Finally, sealing between plastic strips and glass plates is unpredictable. Besides, the junction between side spacers and bottom spacer, or the casting stand has a gap that is very difficult to close. Acrylamide solution often leaks from within the cavity while waiting for gel to polymerize. Attempts to mend leaks during gelling often ends up with unsatisfactory electrophoresis results.

The chemical composition of the gel varies depending on specificity of experiments. Polyacrylamide gel electrophoresis is divided into denatured, partially denatured and non-denatured PAGE categories. Denatured PAGE system is used for protein and nucleic acid studies. For protein molecular weight determinations, the gel and the electrophoresis buffer include a detergent (SDS). In this way, the intra-molecular disulfide bonds of sample proteins are reduced before electrophoresis. In protein chemistry, PAGE in the presence of detergent SDS separates mixture of protein based on the molecular weight. During separation, while applying electrical current, diffusion through gel is minimized. Molecules resolve into narrow bands depend on their mobility in the gel matrix. Protein bands are visualized after staining. The gel is dried for preservation or to continue with other analysis.

The denatured PAGE system is also used in nucleic acid and gene sequencing studies. The sequencing gel contains urea and/or foramide. After electrophoresis separation, radioactive labeled nucleotides are examined under UV light. The gel is also exposed to X-ray film for establishing a permanent record.

A partially denatured PAGE system uses a detergent-containing gel and buffer to assay non-denatured, native proteins. For non-denatured PAGE systems, neither gel nor buffer contains detergent. This is used to assay native proteins.

Most laboratories follow the conventional method for making their own gel (as previously described). All stock solutions except 10% ammonium persulfate are prepared and stored for one to six months. Powdered chemicals, such as acrylamide, bis-acrylamide, tris base, HCl, SDS, ammonium persulfate, TEMED, urea, EDTA, boric acid and foramide, are available commercially for gel-making.

To make the gels described above in conventional way, laboratory personnel have to prepare several stock solutions. Several chemicals used in gel preparation are hazardous and require special cautions during handling. All chemicals used in gel mixture have to be at the highest purity, otherwise, aberrant electrophoresis results may occur. Furthermore, stock solutions take up space from cold storage facility such as refrigerator. On the day of preparing gels, the following procedure takes place:

1). A fresh 10% ammonium persulfate solution is prepared.
2). Precise volumes of five stock solutions are measured out.
3). The solution is mixed and then deaerated under vacuum or aspirator.

Several commercial products such as pre-mixed acrylamide powder, pre-mixed acrylamide solutions, and pre-cast mini-gel are designed to simplify the gel making process. However there are certain drawbacks related to each of the above mentioned products. Premixed powder do not eliminate the potential danger of handling bio-hazardous chemicals. Premixed acrylamide solution at specific gel strength limits the application of electrophoresis. Premixed stock acrylamide solutions are supplied in large volumes (500 ml or more), which does not relief the problem of cold storage space. Limited shelf life of premixed solution means unavoidable wastes. In any case, the fresh 10% ammonium persulfate solution has to be made the day of casting the gel. Pre-cast mini-gel provides convenience for electrophoresis at high cost with a short shelf life and requirement of special storage.

Consequently, a need exists for method of preparing polyacrylamide gel samples for electrophoresis analysis which includes a polyacrylamide formation system which eliminates the potential danger of handling bio-hazardous chemicals, which incorporates the effective and efficient use of premixed chemicals for preparing the acrylamide solution at specific gel strength and without excessive waste, which relieves the problem of cold storage space, and a spacer system for casting polyacrylamide gel which requires a minimum degree of manipulation for assembly together, which effectively seals the two glass plates against leaking, which provides a predetermined thickness of polyacrylamide gel, and which consistently provides satisfactory electrophoresis results.

SUMMARY OF THE INVENTION

The method and system of the present invention overcomes all of the existing needs described above and provides for the formation of with desirable and advantageous properties employing a process which provides the requisite levels of simplicity, reduced cost, and fewer processing steps.

The advantages of the above-described method system for producing a polyacrylamide gel is as follows:

1. It eliminates unnecessary exposure of laboratory personnel to hazardous chemicals during weighing and pipetting.
2. Reproducible result are obtained from experiment to experiment.
3. A ready-to-use gel mixture can be produced which is stable at room temperature for a reasonable amount of time (at least three months). This will make available additional cold storage space in the laboratory.
4. The subject system and method for producing a polyacrylamide gel is compatible with all existing PAGE systems in use in the laboratory. Therefore, there is no need to invest additional capital for new equipment.
5. The gel mixture is ready to degas in less than a minute and saves significant amounts of set-up time (up to many hours).
6. It will save on training time for inexperienced lab technicians since the subject system and method are very user friendly.
7. It enables exploration of many different combinations of electrophoresis equipment without spending on large amounts of money for chemicals and laboratory investigation.
8. It is environmentally sound because the convenient packaging efficiently uses the right amount of chemicals with no wasted stock solutions and with a correspondingly less chance of spillage. The residual gel solution in the container can be readily disposed of after gelling.
9. This invention permits a manufacturer to store chemicals for making polyacrylamide gel in the special container thus preserving the potency of all chemical ingredients for subsequent polymerization.
10. This invention provides a method for easy set up of the glass plates for use as a gel formation chamber. The leak-proof chamber significantly improves the effectiveness of the gel making process.

More specifically, this invention relates to a method and system for producing a polyacrylamide gel sample typically for use in electrophoretic analysis. The subject method comprises providing a container comprising a bottle and cap assembly for conducting a gel formation sequence. The cap assembly includes means defining a storage compartment. A plurality of premixed chemical materials are employed for producing a polyacrylamide gel used to make the gel samples. Preferably, the container comprises a bottle for storing an acrylamide solution and a cap assembly for storing the premixed chemical materials in dry particulate form therewithin. The cap is located atop the bottle. The individual premixed chemical materials are stored in the bottle and in the storage compartment for subsequently producing the acrylamide gel solution in situ within the confines of the container so that the step of transferring of the gel stock solutions to an auxiliary container is avoided.

The premixed chemical materials are introduced into the bottle from the storage compartment by opening the compartment and releasing the chemical materials contained therein into the bottle. Typically, the premixed chemical materials are introduced into an acrylamide solution located in the bottle by breaking open the compartment.

Thereafter, the plurality of individual chemical materials in the bottle are intermixed thereby producing the acrylamide gel solution. More specifically, the premixed chemical materials and the acrylamide solution are intermixed to produce in situ the acrylamide gel solution within the confines of the bottle.

The premixed chemical materials are typically in dry particulate form. In general they comprise a buffer salt and ammonium persulfate with or without a detergent. In a preferred form of this invention, the container further includes an opening at the top of the cap assembly. TEMED, or a like chemical accelerator, can be introduced into the container for completing the gel formation reaction after the premixed chemical materials have been introducing into the bottle. In another preferred form of the present invention, after the intermixing of the plurality of premixed chemical materials in the bottle, and prior to introducing the accelerator, the intermixed chemical materials are deaerated. Deaeration can be accomplished by connecting the container to a water aspirator or through the use of a vacuumed desiccator. A further way to facilitate the deaeration step is by removing the top of the cap assembly.

A method for producing a polyacrylamide gel sample for use in electrophoretic analysis can be produced from the above-described acrylamide gel solution. Means defining a leak-proof formation chamber for casting polyacrylamide gel samples from the acrylamide gel solution are first provided. The leak-proof formation chamber typically comprises a pair of plates each having a pair of major surfaces and a easily-alignable, unitary, substantially U-shaped spacer member.

The U-shaped spacer member comprises a horizontally-extending lower section and a pair of vertically-extending side sections of the U-shaped spacer member. Typically, prior to conducting electrophoresis using the polacrylamide gel sample in the formation chamber, the lower section of the U-shaped spacer member is removed. The present invention is typically designed so that the polyacrylamide gel sample will remain intact.

In one form of this preferred structure, the spacer member includes means defines a slit at the intersection of the lower and side sections, and the lower section includes a tab. The lower section can then be removed from the spacer member by a user pulling on the tab. After the lower section is removed from the U-shaped spacer member, the side sections can remain in place alongside the vertically-extending sides of the polacrylamide gel sample.

In another preferred form of this invention, the spacer member includes several parts. More specifically, the spacer member can comprise a pair of inner vertically-extending side members and an integral outer U-shaped spacer member comprising a horizontally-extending lower section and a pair of vertically-extending side sections. The inner portion of the inner vertically-extending side members are adjacent to the sides of the acrylamide gel sample. The outer portion of the inner vertically-extending side members are adjacent to the inner portion of the vertically-extending side sections of the U-shaped spacer member. After the polyacrylamide gel sample is formed, the outer U-shaped member can be readily removed. This leaves the inner vertically-extending side members intact adjacent to the vertical sides of the polyacrylamide gel sample.

In forming the polyacrylamide gel sample, the plates are first positioned so that a major surface of each plate is adjacent one to the other with the spacer member located between the plates at the bottom and sides thereof. A formation chamber, generally rectangular in shape, is thereby created between the plates for casting polyacrylamide gel samples. This plates-spacer member assembly can be held in place by fastening means such as clamps or the like. Once the plates-spacer member assembly is completed, the acrylamide gel solution is introduced into the formation chamber. The polyacrylamide gel sample is then cast in the formation chamber. The polacrylamide gel sample remains in the formation chamber in an intact condition for use in, for example, electrophoretic analysis. Preferably, the polacrylamide gel sample has a substantially uniformly even thickness.

The foregoing and other objects, features and advantages of the invention will become more readily apparent from the following detailed description of a preferred embodiment.

DESCRIPTION OF THE DRAWINGS

FIG. 1 is a perspective view of a container of the present invention which comprises a mixing bottle and a cap assembly including a compartment for storing premixed ingredients for producing an acrylamide gel solution.

FIG. 2 is an exploded perspective view of an acrylamide gel sample formation system comprising a leak-proof formation chamber including a pair of plates and a unitary U-shaped spacer member.

DETAILED DESCRIPTION OF A PREFERRED EMBODIMENT

Figure 3:
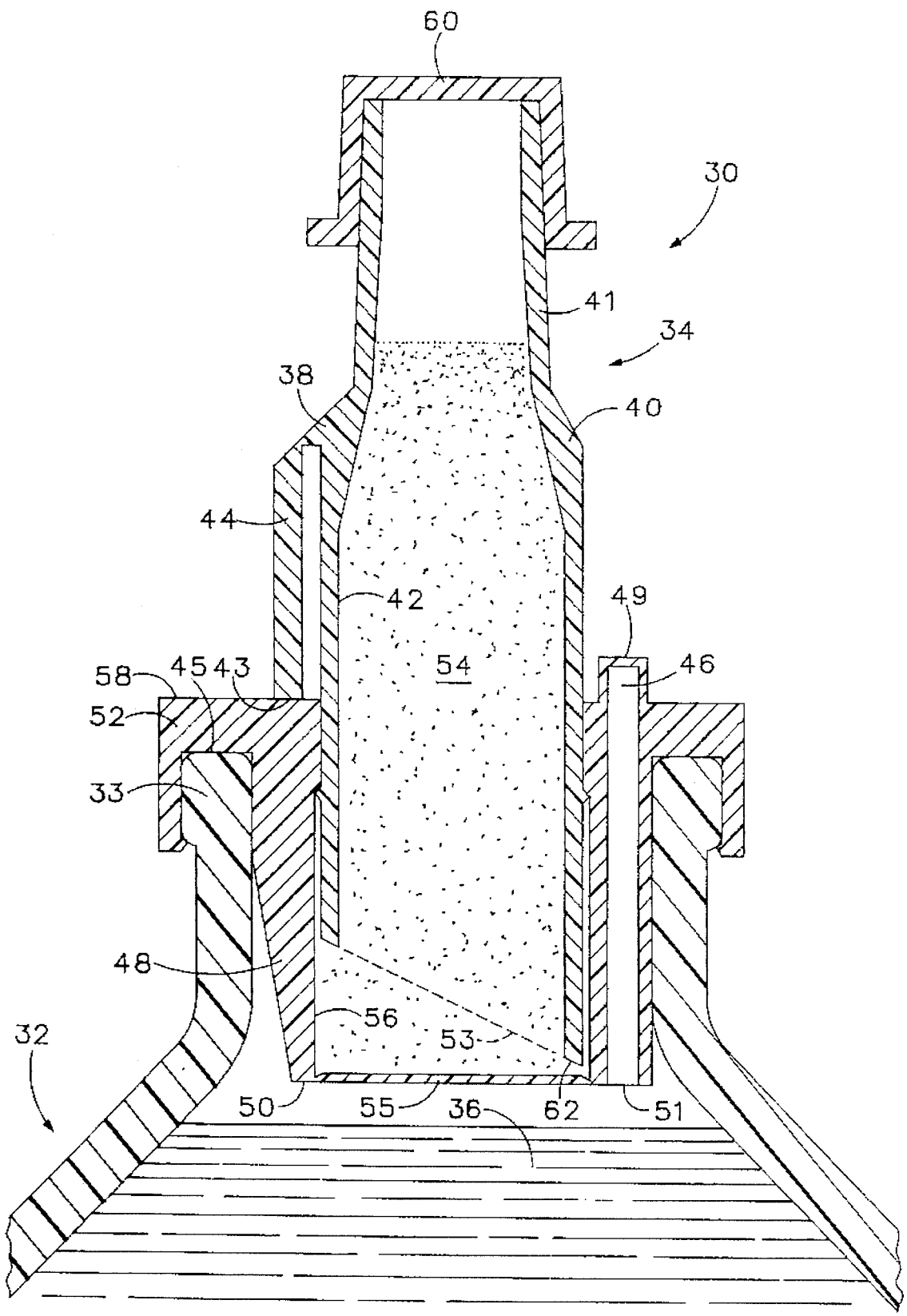
FIG. 3 is a sectional view of the mixing bottle and cap assembly of FIG. 1 in storage.
Figure 4:
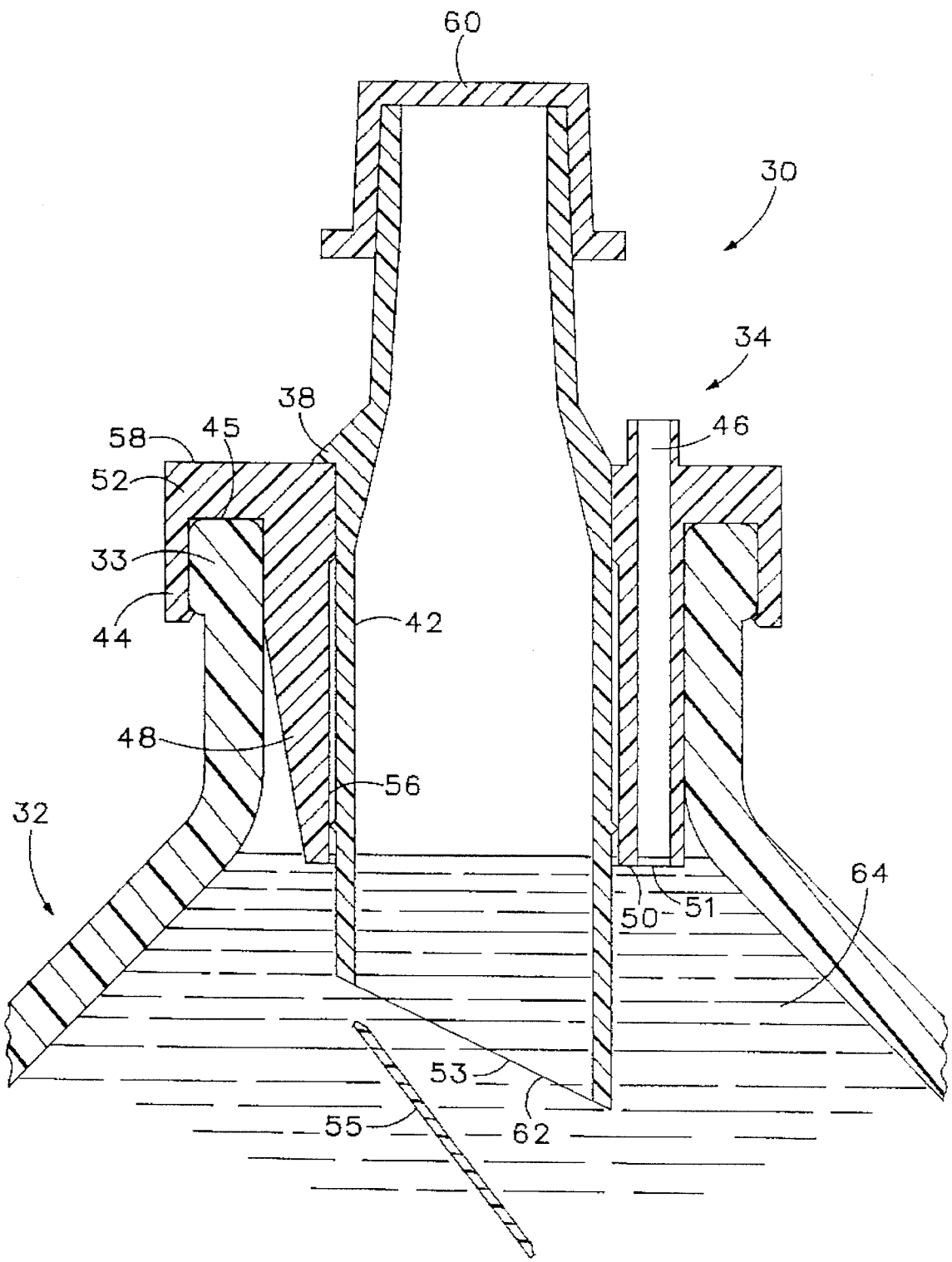
FIG. 4 is a sectional view of the mixing bottle and cap assembly of FIG. 1 after the stored materials have been intermixed.

Referring now to FIGS. 1, 3 and 4, the container system 30 of the present invention provides for a bottle 32 having a rim 33 and a cap assembly 34. The bottle 32 is typically made of glass, an amber glass bottle being the preferred choice.

The bottle contains an acrylamide solution 36 (acrylamide and bis-acrylamide) of an appropriate strength. The total amount of solution varies depending on the type of gel which is produced. For example, the preferred total amount solution for making a mini-gel is between about 7.5 and 15 ml; for making a regular size gel is between about 15 and 50 ml; and for making a sequencing gel is between about 50 and 80 ml. Since a volume of the chemical mixture needs to be accounted for, the amount of acrylamide solution 36 is less than the volume of acrylamide gel solution 54. A representative formulation is shown in Example 2 below. Regarding the ratios of acrylamide:bis-acrylamide, the typical ratio for protein gel is from about 40:1 to 20:1, and preferably from about 37.5:1 to 29:1, and for sequencing gel from about 25:1 to 15:1, and preferably about 19:1.

A specially designed cap assembly 34 holds a powder mixture of premixed chemical materials 54 for use in the polyacrylamide gel formation process. The cap assembly 34 has three parts as shown in FIGS. 3 and 4, namely, an elongate tubular housing 40, a sleeve 48 and a cap 60. The cap assembly 34 is inserted into the mouth of the bottle 32 and is maintained in place atop the rim 33 thereof.

As best seen in FIG. 3, elongate tubular housing 40 defines an inner chamber 42 for storing individual premixed chemical materials 54. Intermixed chemical materials 54 are typically a buffer salt and ammonium persulfate if a non-denatured gel is to be produced. If a denatured gel is to be the final product, a detergent such as SDS (sodium dodecyl sulfate), is added to the system. The buffer salt is generally a "Tris" buffer, namely, a mixture of 2-amino- 2(hydroxymethyl)-propane-1,3-diol and (Tris[hydroxymethyl] aminomethane hydrochloride), to a pH of 8.8. The tubular housing 40 narrows at its upper portion to form a narrowed neck 41 and has a pointed end section 62 at its lower end 53. An outer flange 44 is attached to the housing 40 at a point below the narrowed neck 41 via an outer edge section 38. The tubular housing 40 is mounted within the inner cylindrical chamber defined by an outer sleeve 48. Outer sleeve 48 defines an inner chamber 56 which has a lower end 50. Cap bottom 55, extends from the lower end 50 to close off inner chambers 42 and 56 so that chemical materials 54 are retained therewithin during storage. At the top of sleeve 48 is a rim 52 which defines an inner flange 45. The inner flange 45 is sized to engage and to be supported by the rim 33 of bottle 32. During storage of the premixed chemical materials in cap assembly 34 and the acrylamide solution 36 in bottle 32, the lower edge 43 of outer flange 44 is disposed on the top 58 of rim 52 of sleeve 48 so as to prevent downward movement of tubular housing 40 relative to sleeve 48 and bottle 32. Sleeve 48 also includes a vertically-extending vent channel 46 which is closed at its upper end 49 and is opened at its lower end 51.

As best seen in FIG. 4, the acrylamide gel solution 64 of the this invention can be prepared in the container system 30 by introducing the premixed chemical materials 54 in cap assembly 34 into the acrylamide solution 36. This is accomplished by detaching the outer flange 44 from the tubular housing 40 leaving outer edge section 38 intact. With outer flange 44 removed, the tubular housing 40 can be pushed downwardly toward bottle 32, until the edge section 38 engages the top 58 of rim 52, so that the pointed end section 62 pieces breaks open cover 50 from its position attached to lower end 55. This in turn releases the premixed chemical materials 54 from within inner chamber 42 and into acrylamide solution 36. The powder dissolves readily with gentle shaking. Next, upper end 49 of the vent 46 is removed from atop tubular housing 40 and TEMED, or a like accelerator material, is introduced into tubular housing 40, and then into acrylamide gel solution 64 for completing the gel formation reaction. If desired, after intermixing of the premixed chemical materials in the bottle 32, and prior to introducing the TEMED, the intermixed chemical materials can be deaerated after removing the cap 60 on top of tubular housing 40 and then connect the neck 41 to a water aspirator or place container system 30 into a vacuumed desiccator. After introducing TEMED into the deaerated acrylamide gel solution, pouring the solution out of housing 40 into glass plate assembly can be facilitated by creating vent 46 by first removing upper end 49. In any case, the acrylamide gel solution 64 of the present invention is thus produced ready for formation into a gel sample.

Figure 5:
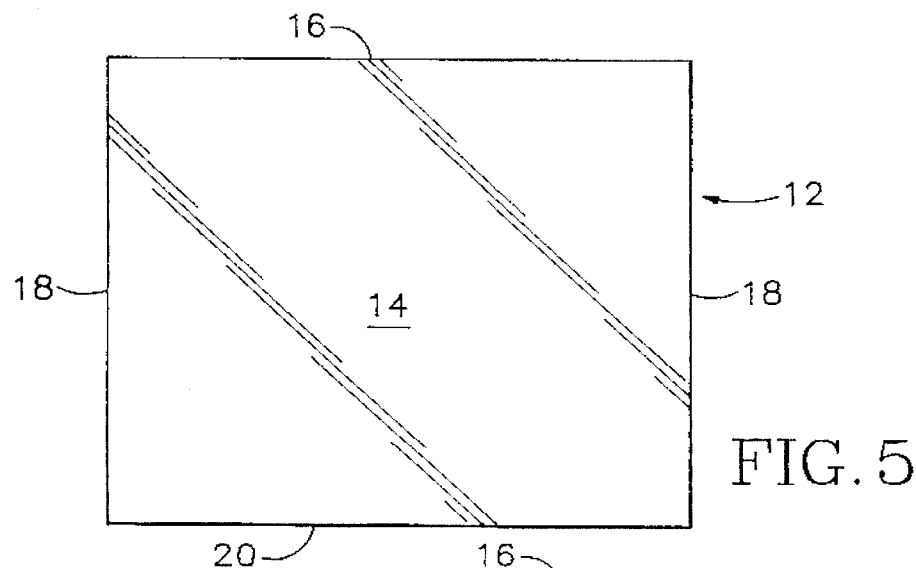
FIG. 5 is a front elevational view of plate 14 of FIG. 2.
Figure 6:
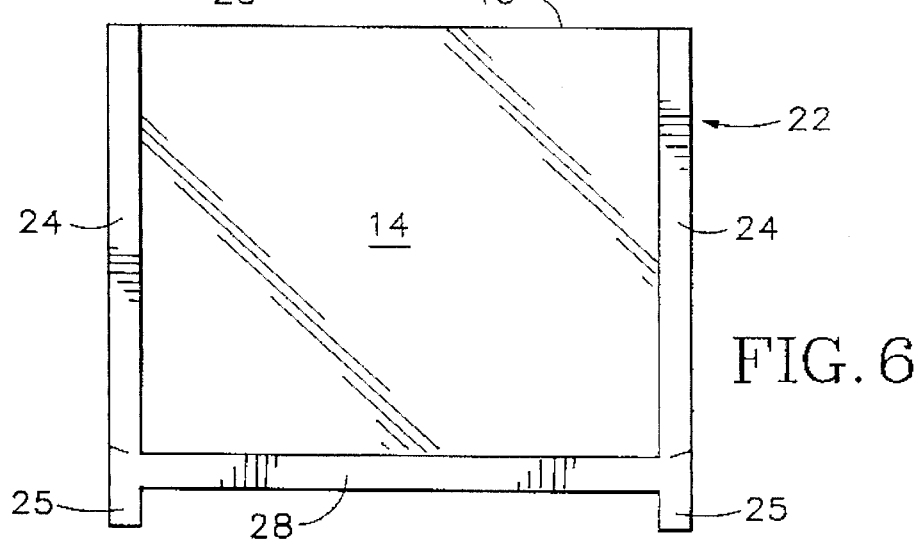
FIG. 6 is a front elevational view of the space member assembly comprising the spacer member and glass plates of FIG. 1 in place so that a leak-proof formation chamber is formed therebetween.
Figure 7:
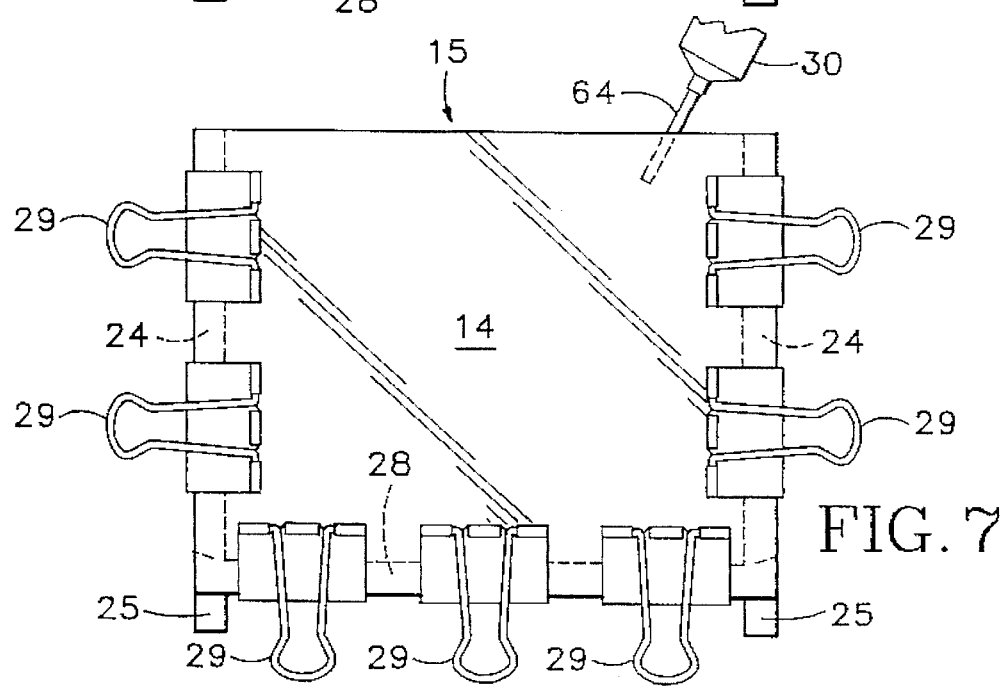
FIG. 7 is a front elevational view of the spacer member assembly of FIG. 6 with clips 29 in place and having an acrylamide gel solution being introduced into the leak-proof formation chamber.
Figure 8:
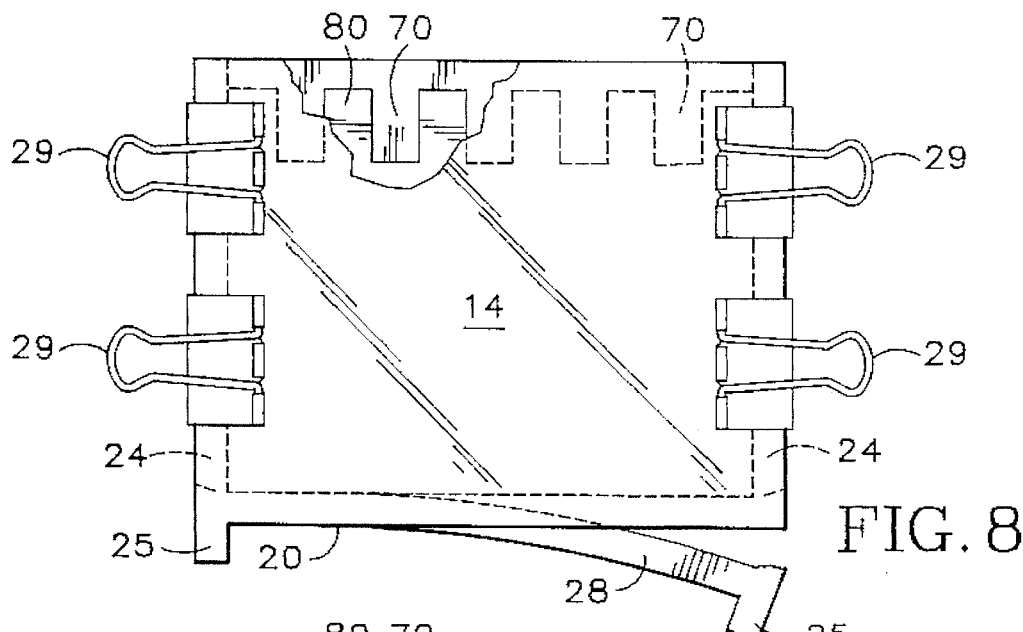
FIG. 8 is a front elevational view of the spacer member assembly of FIG. 7 with polyacrylamide gel sample having been formed, the clips 29 at the bottom of the assembly removed, a template comb in place, and the lower spacer section being removed.

Referring now to FIG. 2, a leak-proof formation chamber system 10 for casting polyacrylamide gel samples from a polyacrylamide gel is provided. The system 10 includes a easily-alignable, unitary, substantially U-shaped spacer member 22 and a pair of plates 12. The plates 12, which are generally made of glass, comprise major surfaces 14, and top, side and bottom portions 16, 18 and 20, respectively (see FIG. 5).

The spacer member 22 is formed from either silicon or plastic materials of different thickness. The side sections 24 have an inner edge 26 and bottom section 28 includes pull tabs 25 at its outer ends for purposes of subsequent removal of the bottom section after gel formation is completed. A slit 27 is cut at the intersection of side and bottom sections of the spacer member. The dimension of U-spacer member are tailored to fit different electrophoresis systems available on the market. For example, here are the dimensions for some of the most common products on the market used in electrophoresis apparatus: Bio-Rad (16×16 cm, 16×20 cm, 10.2×8.3 cm), Owl Scientific (11×10 cm, 16×14 cm), Hoefer (10×12 cm, 14×16–32 cm).

Figure 9:
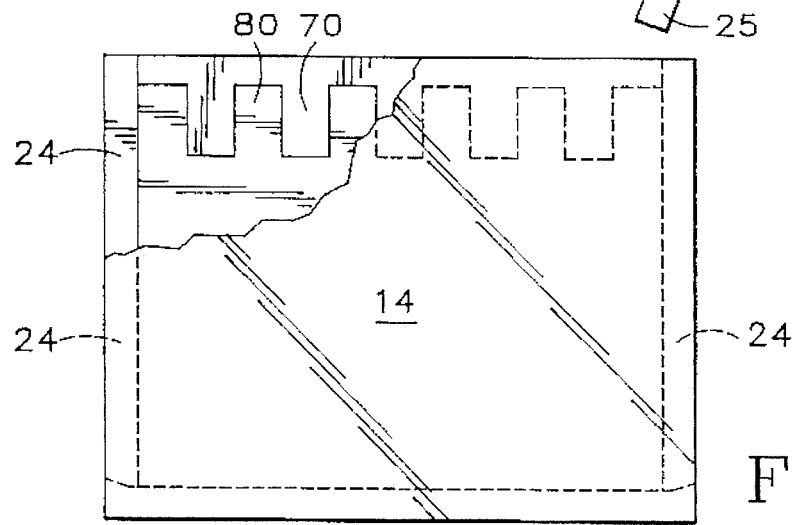
FIG. 9 is a front elevational view of the spacer member assembly of FIG. 8 with the clips 29 at the sides of the assembly and the lower spacer section removed ready for use in electrophoretic analysis.

FIGS. 5–10 demonstrates how to assemble plates. First, the spacer member 22 is placed onto one of the glass plate 12 (see FIG. 6). Then, the top plate 12 is placed in position, the assembly secured together by clamps 29, and the acrylamide gel solution 64 is poured from the container system 30 into the chamber 15 formed between the glass plates 12 and the polyacrylamide gel sample 80 is formed. An appropriate comb 70 is inserted in place and, after completing the polymerization reaction, clamps 29 located along the bottom 20 of the plate 12 are removed. Tabs 25 are then pulled away from the bottom 20 of the plate 12 to tearing the bottom section 28 of the spacer member 20 away it from the adjacent side sections 24 (see FIG. 8). The remaining clamps 29 attached to the sides 18 of plate 12 are removed and the system as shown in FIG. 9 is ready for electrophoresis.

Figure 10:
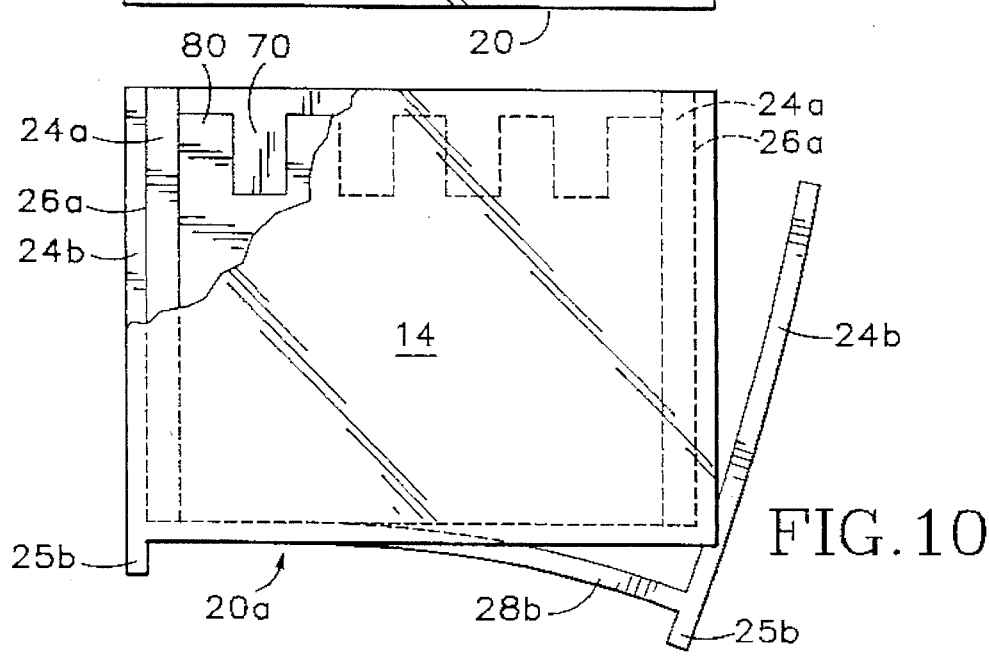
FIG. 10 is a front elevational view of an alternative spacer member assembly comprising a pair of inner side spacer members 24a and circumscribed within an outer U-shaped spacer member 24b which is being removed.

Another form of the spacer member 20 of this invention is shown in FIG. 10. This spacer member 20a includes a one-piece silicon or plastic U-shaped gasket spacer member, similar to the one described above, having side sections 24b, bottom section 28b and tabs 25b. Typically, the width of the U-shaped spacer member for a mini-gel is one cm or less, and for other size gel is 2 cm or less. Also, side spacers 24a are provided which are laid along on the inner edges 26b of side sections 24b. The plates 12 are clamped together as before and the gel cast as described above. The U-shaped gasket spacer member is pulled away from the system before electrophoresis. The side spacers 24a remain in place adjacent to the gel sample 80. Once the U-shaped member is removed, the system as shown in FIG. 10 is ready for electrophoresis.

EXAMPLE 1

Polyacrylamide gel samples were produced using a conventional formation procedure, as follows:

The gel were first prepared with the following stock solutions:

A. Acrylamide/Bis (30% T, 2.67% C)

B. 1.5 M Tris(2-amino-2-(hydroxymethyl)propane- 1,3-diol) and HCl, pH 8.8

C. 0.5 M Tris and HCl, pH 6.8

D. 10% SDS

E. 10% ammonium persulfate, prepared fresh daily

F. TEMED

Working Solutions of different gel strength:

|  | Stock | | | | |
| --- | --- | --- | --- | --- | --- |
| Solutions | 15% | 12% | 10% | 7.5% | 4% |
| Dist. Water | 2.35 | 3.35 | 4.02 | 4.85 | 6.02 |
| Soln. A, ml | 5.0 | 4.0 | 3.33 | 2.5 | 1.33 |
| Soln. B, ml | 2.5 | 2.5 | 2.5 | 2.5 | — |
| Soln. C, ml | — | — | — | — | 2.5 |
| Soln. D, µl | 100 | 100 | 100 | 100 | 100 |
| Soln. E, µl | 50 | 50 | 50 | 50 | 50 |
| Soln. F, µl | 5 | 5 | 5 | 5 | 10 |

Gel mixtures were prepared by mixing the above listed stock solutions in descending order except solution F. The mixture was deaerated for at least 15 minutes. Solution F was added by pouring it into the space in between glass plate-spacer member assembly where it is cast as a gel. A comb was then inserted in between glass plates. After the gel solidified, it was ready for electrophoresis. A 4% stacking gel was cast on top after initial gel formation at a predetermined height. The stacking gel solidified after an additional 45 to 60 minutes

EXAMPLE 2

Polyacrylamide gel samples were produced using the in situ procedure of the present invention.

Bottle 32 was employed which contained acrylamide solution 36 for preparing 10 ml of 15% acrylamide gel solution. The solution contained 1.45 gm acrylamide and 0.05 gm bis-acrylamide in 9.71 ml of water. The cap assembly 34 contained 0.5056 gm of premixed chemical materials 54. Chemical materials 54 comprised 0.3421 gm Tris base, 0.1484 gm Tris HCl, 0.0051 gm ammonium persulfate, and 0.01 gm SDS. Solution 36 and chemical materials 54 were pre-packed in container system 30 and the package was storable but nevertheless readily available for making a 15% mini-size polyacrylamide gel without making and premixing solutions A–E as provided in Example 1 above.

The acrylamide gel solution was constituted by pushing cap assembly 40 down breaking open cap bottom 55 of sleeve 48. Chemical material 54 was thus released into bottle 32 and readily dissolved in the acrylamide solution 36 to form acrylamide gel solution 64. Cap 60 was removed, and container system 30 put into a desiccator and deaerated for 15 minutes. 5 µl TEMED were added into the acrylamide gel solution 64.

A polyacrylamide gel was then cast from the acrylamide gel solution 64 as described above in Example 1.

Having illustrated and described the principles of my invention in a preferred embodiment thereof, it should be readily apparent to those skilled in the art that the invention can be modified in arrangement and detail without departing from such principles. We claim all modifications coming within the spirit and scope of the accompanying claims.

I claim:

1. A method for producing a polyacrylamide gel sample for use in electrophoretic analysis, comprising providing a container comprising a bottle including a first storage compartment for storing an acrylamide solution, and a cap assembly located atop said bottle including a second storage compartment for storing chemical materials for producing a polyacrylamide gel;

introducing the acrylamide solution into the first storage compartment and the chemical materials into the second storage compartment;

storing the chemical materials in said second storage compartment and said acrylamide solution in the first storage compartment for subsequently producing said acrylamide gel solution in situ within the confines of said container;

subsequently opening said second storage compartment and introducing said chemical materials contained therein into said bottle;

intermixing said chemical materials and said acrylamide solution in said bottle thereby producing said acrylamide gel solution;

providing means defining a leak-proof formation chamber for casting polyacrylamide gel samples from said acrylamide gel solution, said leak-proof formation chamber comprising a pair of plates each having a pair of major surfaces and a easily-alignable spacer member, said plates being positioned so that a major surface of each plate is adjacent to the other with the spacer member located between said plates thereby defining said formation chamber for casting polyacrylamide gel samples; introducing said acrylamide gel solution into said formation chamber; and forming said polyacrylamide gel sample in said formation chamber in an intact condition for use in electrophoretic analysis.

2. The method of claim 1, wherein spacer member comprises providing a unitary, substantially U-shaped spacer member including a removable horizontally-extending lower section and a pair of vertically-extending side sections of said U-shaped spacer member, and prior to conducting said electrophoretic analysis, removing said horizontally-extending lower section of said U-shaped spacer member.

3. The method of claim 2, wherein said spacer member includes means defining a slit at the intersection of said lower and side sections and said lower section includes a tab, said lower section being removed from the spacer member by a user pulling on the tab.

4. The method of claim 2, wherein after said lower section is removed from said U-shaped spacer member, said side sections remaining in place adjacent to said polyacrylamide gel sample.

5. The method of claim 1, wherein said polyacrylamide gel sample has a substantially uniform even thickness.

6. The method of claim 1, wherein said chemical materials are stored in said second compartment in dry particulate form.

7. The method of claim 6, wherein said chemical materials in dry particulate form comprise buffer salts and ammonium persulfate with or without a denaturing agent.

8. The method of claim 1, wherein said container further includes an opening at the top of said cap assembly for introducing a polymerization accelerator into the container after chemical materials have been introducing into the bottle.

9. The method of claim 8, wherein after said intermixing of said chemical materials in said bottle, and prior to introducing said polymerization accelerator, deaerating said intermixed chemical materials.

10. The method of claim 9, wherein said deaerating step is conducted removing the top of said cap assembly.

11. The method of claim 1 for producing a polyacrylamide gel sample for use in electrophoretic analysis which further comprises providing a pair of plates each having a pair of major surfaces and a spacer member comprising an easily-alignable, unitary, substantially U-shaped spacer member including a horizontally-extending lower section having an upper and a lower edge and a pair of vertically-extending side sections of said U-shaped spacer member, each of said vertically-extending side sections having an upper and a lower end, the lower ends of the vertically-extending side sections being joined to the upper edge of said horizontally-extending lower section, said plates being positioned so that a major surface of each plate is adjacent to the other with the spacer member located between said plates thereby defining said formation chamber for casting polyacrylamide gel samples;

introducing said acrylamide gel solution into said formation chamber, the solution flowing into the U-shaped spacer member from the upper end of the vertically-extending side sections and being retained within the U-shaped spacer member during the formation of said polyacrylamide gel sample; and after forming said polyacrylamide gel sample in said formation chamber in an intact condition for use in electrophoretic analysis, removing said lower section of said U-shaped spacer member, subsequent to formation of said polyacrylamide gel sample, and prior to electrophoretic analysis on said polyacrylamide gel sample in said formation chamber.

12. The method of claim 11, wherein said spacer member comprises a pair of vertically-extending side sections disposed adjacent to vertically-extending sides of said polyacrylamide gel sample and a unitary, substantially U-shaped spacer member including a horizontally-extending lower section and a pair of vertically-extending side sections, said U-shaped spacer member circumscribing said pair of vertically-extending side sections, and prior to conducting electrophoretic analysis with said polyacrylamide gel sample, the horizontally-extended lower spacer of the said U-shaped spacer member is removed.

13. The method of claim 11, wherein said spacer member includes means defining a slit at the intersection of said lower and side sections and said lower section includes a tab, said lower section being removed from the spacer member by a user pulling on the tab.

14. The method of claim 11, wherein after said lower section is removed from said U-shaped spacer member, said side sections remain in place alongside said polacrylamide gel sample.

15. The method of claim 11, wherein said polyacrylamide gel sample has a substantially uniform even thickness.

* * * * *